United States Patent [19]

Parker

[11] 4,114,038

[45] Sep. 12, 1978

[54] PHOTOELECTRIC SENSING HEAD WITH WIPING MEANS

[75] Inventor: Adrian Roger Parker, St. Austell, England

[73] Assignee: Partech (Electronics) Limited, England

[21] Appl. No.: 784,415

[22] Filed: Apr. 4, 1977

[30] Foreign Application Priority Data

Apr. 7, 1976 [GB] United Kingdom ............... 14091/76

[51] Int. Cl.² ............................................. H01J 5/02
[52] U.S. Cl. .................................... 250/239; 356/208
[58] Field of Search ....................... 250/239, 373, 455; 356/208

[56] References Cited

U.S. PATENT DOCUMENTS 2,866,379  12/1958  Veit ........................................ 356/208
2,892,378  6/1959  Canada ................................... 356/208
3,731,091  5/1973  Rosso et al. ........................... 250/373

Primary Examiner—David C. Nelms
Attorney, Agent, or Firm—Watts, Hoffmann, Fisher & Heinke Co.

[57] ABSTRACT

A sensing head for use in turbidity measurements has a body with a sensing surface, for example a photocell enclosure, which is immersed in liquid in use of the head. Periodic cleaning of the sensing surface is effected by powered movement, for example under control of an electric motor, of the body relative to a housing in which a wiping element such as an O-ring is seated. As applied to a photoelectric head a further body enclosing a light source may be mounted for movement with the photocell enclosure to be wiped clean by a separate wiping element in the housing.

17 Claims, 6 Drawing Figures

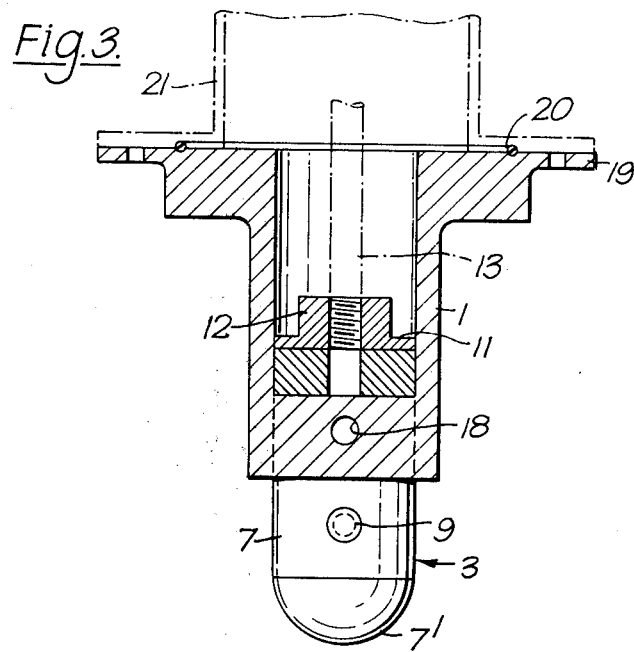
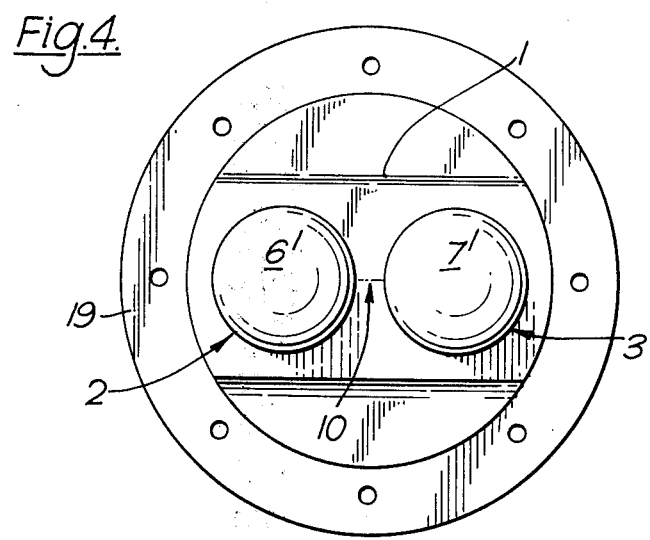

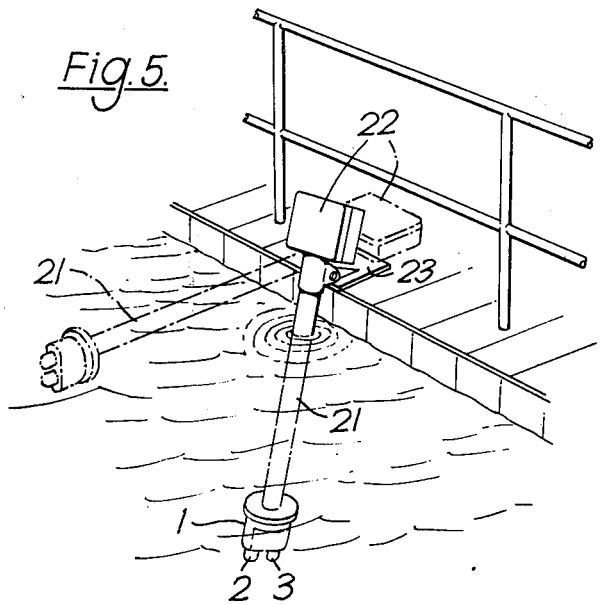
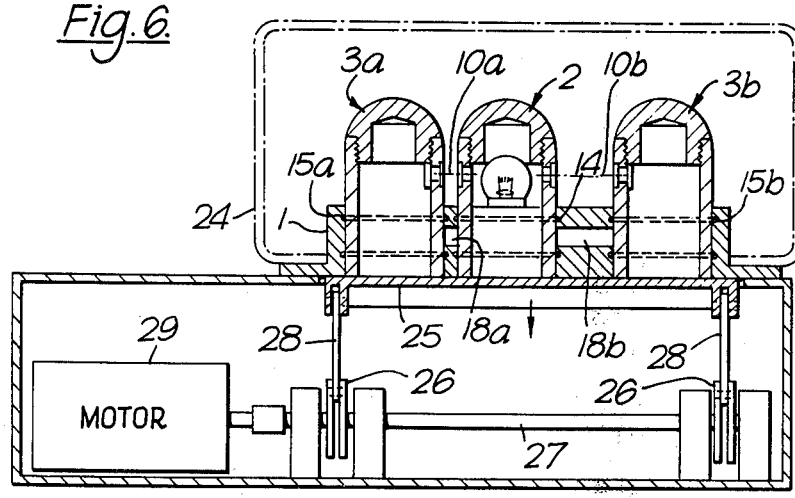

PHOTOELECTRIC SENSING HEAD WITH WIPING MEANS

This invention relates to photoelectric sensing heads, with particular, but not exclusive, reference to photoelectric sensing heads for use in turbidity measuring instruments.

Turbidity measuring photoelectric sensing heads are known in which a light source and a photocell are separated by a space containing a liquid the turbidity of which is to be measured. The photocell is arranged to measure either the light transmitted through the liquid in the space or light scattered by this liquid, according to the degree of turbidity of the liquid. Light from the source passes into the liquid by way of a light transmitting wall or window, and enters the photocell through a further light transmitting wall or window.

A practical problem associated with the use of turbidity measuring sensing heads of the kind referred to above is that of contamination of the light transmitting walls or windows associated with the light source and the photocell. In the course of time a turbid liquid will cause a deposit to form on the surfaces of the light transmitting walls or windows, upsetting the accuracy of the turbidity measurement. The present invention provides an improved photoelectric sensing head in which this difficulty can be avoided.

According to the present invention there is provided a photoelectric sensing head comprising a source unit and at least one photocell unit arranged side by side in a common housing, each unit having an enclosure with a light transmitting wall or window, the housing having wiping elements which made wiping contact with the light transmitting walls or windows of the enclosures, and means for displacing the enclosures relative to the housing to cause the wiping elements to pass over the surfaces of the said walls to clean them.

By displacing the enclosures relative to the housing the light transmitting walls or windows of the enclosures can be wiped clean, without any need to remove the sensing head from a liquid in which it may be immersed, and without the need to remove or have access to the head itself.

Preferably the enclosures housing the source unit and the photocell unit have cylindrical walls, the wiping elements comprising resilient rings seated in the housing and making contact with said walls.

In one embodiment of the invention two said photocell units are arranged an opposite sides of the source unit, the photocell units in operation of the head receiving light from the source unit through the respective light transmitting walls or windows.

The enclosures are preferably movable between retracted positions within the housing and extended positions, projecting beyond the housing, in which the or each photocell unit is separated from the source unit by a gap which is traversed by light from the source unit in use of the head.

When measuring liquid turbidity the liquid under test is disposed in or flows through the gap when the enclosures are in their extended position.

The sensing head according to the invention can conveniently provide for regular calibration of the or each photocell unit. Thus the or each photocell unit may be separated from the source unit by a calibration gap within the housing in the retracted positions of the enclosures, the or each calibration gap being effectively sealed from the exterior by the wiping elements which in practice make sealing peripheral contact with the enclosures. The housing may additionally be provided with seals contacting the surfaces of the enclosures within the housing at positions on the other side of the calibration gap or gaps from the wiping elements.

The enclosures may be mechanically interconnected for movement together by the displacement means. Conveniently, the means for displacing the enclosures comprises a member connected to the enclosures and displaceable by a reversible motor. For example a motor-driven screw may extend axially through the housing and engage a nut attached to the enclosures, so that rotation of the screw effects axial displacement of the enclosures, relative to the housing, in a direction dependent upon the direction of rotation of the screw.

A photoelectric sensing head according to the invention may be provided with more than one photocell unit defining two or more gaps for turbidity measurement either by comparative measurement of light transmission or light scattering. The light source employed in the source unit may be of any convenient type, according to the degree of turbidity of the liquids under examination. For example the source may comprise an ultraviolet, a discharge flash tube or a white tungsten filament source.

The invention is not limited in its practical applications to photoelectric sensing heads, but is in general applicable to other types of sensor having surfaces which have to be kept clean and free from contamination or soiling when immersed in liquid. For example, thermometers, conductivity meters, pH meters and dissolved oxygen meters employed in connection with pollution monitoring instruments may all have sensing surfaces which are immersed in liquid in use of a sensing head. It is a further object of the invention to provide a self cleaning sensing head which enables such cleaning of sensing heads to be effected automatically.

According therefore to another aspect of the invention there is provided a self-cleaning sensing head comprising a body having a sensing surface, a housing in which the body is mounted for relative displacement, wiping means within the housing making wiping contact with the sensing surface of the body, and powered means for displacing the body relative to the housing between a retracted position in which the sensing surface is within the housing and an extended position in which the sensing surface projects from the housing for immersion in a liquid, movement of the body between said positions causing the sensing surface to be wiped by the wiping means.

The sensing surface is preferably cylindrical, in which case the wiping means may comprise at least one resilient O-ring located within the housing and making wiping contact with the said sensing surface.

The invention will be further described, by way of example only, with reference to the accompanying purely diagrammatic drawings, in which:

FIG. 3 is a diagrammatic axial section taken on line III—III of FIG. 1;

FIG. 4 is a bottom plan view of the sensing head;

FIG. 5 illustrates a typical mounting arrangement for a sensing head of the kind shown in FIGS. 1 to 4; and FIG. 6 is a diagrammatic axial section similar to FIG. 1 of a sensing head according to another embodiment of the invention.

Figure 1:
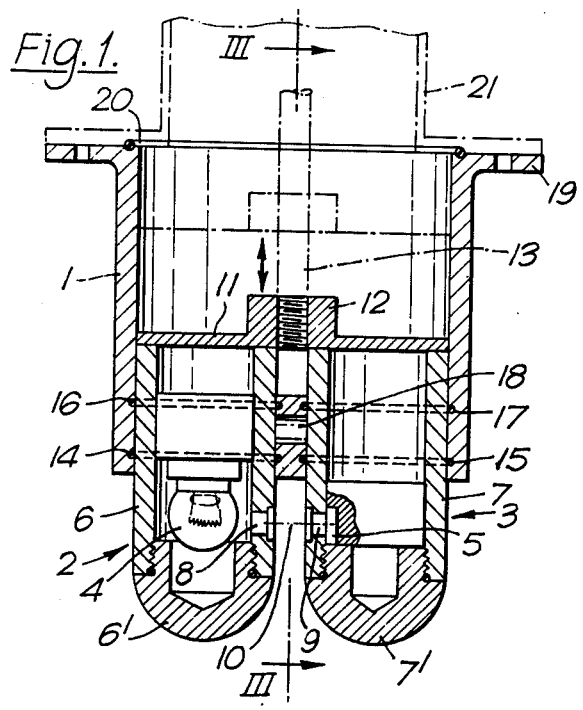
FIG. 1 is a diagrammatic axial section through a photoelectric sensing head according to one embodiment of the invention having a single source and a single photocell.

The illustrated photoelectric sensing head comprises a tubular brass housing 1 in which a source unit 2 and a photocell unit 3 are arranged side-by-side. In the illustrated embodiment the source unit 2 houses a single tungsten filament light bulb source 4, and the photocell unit 3 houses a single photocell 5.

The source unit 2 and the photocell unit 3 are housed in respective hermetically sealed enclosures having cylindrical brass walls 6, 7 respectively which are a sliding fit in respective circular holes formed in the end of the housing 1. Adjacent portions of the two cylindrical walls 6, 7 are provided with respective circular light transmitting and pressure resistant lenses 8, 9, having part-cylindrical outer surfaces flush with the outer surfaces of the walls 6, 7, between which a gap 10 is defined. Light from the source unit 2 is focused by the lens 8 into a beam which traverses the gap 10, the lens 9 focusing the light beam onto the surface of the photocell 5.

In an alternative arrangement the cylindrical walls 6, 7 may be made of "pyrex" (Registered Trade Mark) glass tube or other transparent material and the lenses 8, 9 either dispensed with or mounted within the walls 6, 7.

The two enclosures 2, 3 are interconnected within the housing 1 by a connector plate 11 which is provided centrally with a screw-threaded nut 12 engaged by a rotatable screw-threaded drive shaft 13 extending axially through the housing 1. The shaft 13 is rotatable in either direction by a reversible electric motor (not shown), acting on the shaft 13 either directly or through a suitable drive transmission. By appropriate rotation of the drive shaft 13 the two enclosures 2, 3 are movable in unison axially relative to the housing 1 between a fully extended position, as shown in FIGS. 1 and 3, and a retracted position (not shown) in which the two enclosures 2, 3 are partially withdrawn into the housing 1.

The two circular holes at the free end of the housing 1 in which the cylindrical walls 6, 7 slide are formed with respective internal circumferential grooves in which respective wiping elements in the form of respective resilient O-rings 14, 15 are seated, these rings making contact with the entire circumference of each respective cylindrical wall 6, 7 so that as the walls slide past the rings they are wiped clean. The two O-rings 14, 15 also serve as sliding seals, preventing the ingress of liquid into the housing 1.

Within the housing 1, and spaced from the free end thereof, are two further circular or cylindrical seats in which the respective cylindrical walls 6, 7 slide, these seats being formed with peripheral internal grooves in which respective sealing rings 16, 17 are located to make sealing contact with the respective cylindrical walls.

In the retracted position of the two enclosures 2, 3 the two lenses 8, 9 are located in the space between the O-rings 14, 15 and the sealing rings 16, 17 this space constituting in effect a calibration gap 18. Since the two O-rings 14, 15 automatically wipe the surfaces of the cylindrical walls 6, 7 clean upon retraction of the enclosures 2, 3 the two windows 8, 9 will always be clean and substantially free of contamination when located at the calibration gap 18. The calibration gap 18 may contain a reference liquid or a filter of predetermined density so as to allow accurate and consistent calibration and recalibration of the photocell 5 upon each retraction of the twin enclosures 2, 3. The calibration gap 18 and one of the lenses 9, is illustrated in FIG. 3.

Figure 2:
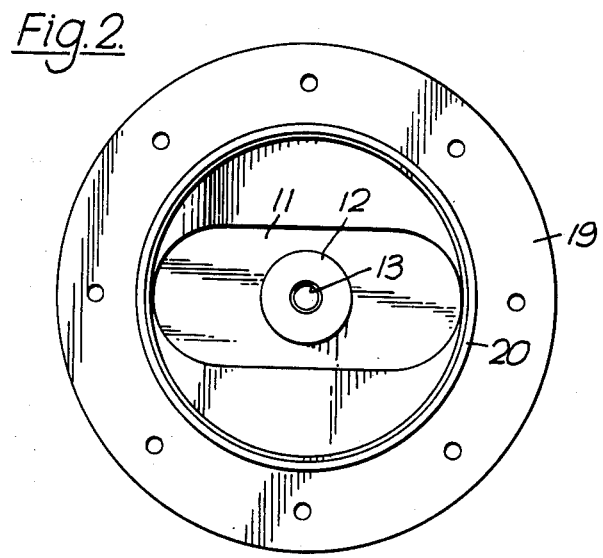
FIG. 2 is a top plan view of the head shown in FIG. 1.

The exterior of the housing 1 is elongate in a direction parallel to the plane containing the axes of the two cylindrical walls 6, 7 of the enclosures 2, 3, as shown in FIGS. 2 and 4. This imparts a streamlined shape to the head, which is formed at its upper end with a circular flange 19 by means of which the head may be bolted, with the interposition of an O-ring seal 20, to a flange end of a supporting tubular boom 21, part of which is shown in broken outline in FIGS. 1 and 3.

The free ends of the two cylindrical walls 6, 7 of the two enclosures, shown lowermost in the drawings, are provided with hermetically sealed removable brass caps 6', 7' respectively of hermispherical shape. Removal of these caps affords easy access to the source 4 and photocell 5 for servicing and replacement.

FIG. 5 shows a typical practical mounting arrangement for a turbidity meter employing a sensing head according to the invention. The sensing head housing 1 is shown carried at the end of the tubular boom 21 through which electrical connections pass to a turbidity measuring instrument 22. The tubular boom 21 is hinged to a mounting 23 above the level of a liquid to enable it to swing about a horizontal axis between an operative position, as shown, in which the housing 1 is fully immersed in the liquid to be monitored and a retracted position, shown in broken outline, in which the axis of the tubular boom 21 is horizontal and the housing 1 is clear of the liquid surface. The drive shaft 13 extends axially through the tubular boom 21 and is connected to a reversible motor (not shown) housed in the unit 22.

FIG. 6 illustrates an alternative embodiment of a sensing head according to the invention having a central source unit 2 and two photocell units 3a and 3b disposed on opposite sides of the source unit 2 and separated therefrom by respective sensing gaps 10a and 10b of different sizes, to enable a comparative measurement to be made when a liquid under examination flows through the gaps.

The common housing 1 in this embodiment is sealed in one wall of a sampling channel 24, shown in broken outline, through which a liquid under test flows. The sealed enclosures of the three units 2, 3a and 3b are attached to a common displaceable carrier 25 which is displaceable by means of a crank mechanism consisting of two cranks 26 mounted on a crankshaft 27 and coupled to the carrier by connecting rods 28. The crankshaft 27 is rotated by means of an electric motor 29 to cause reciprocation of the carrier 25 and therefore of the units 2, 3a and 3b, relative to the housing 1. By this means cleaning of the sensing head can be effected automatically upon energisation of the motor 29.

Analogously with the embodiment of FIGS. 1 to 4, the embodiment of FIG. 6 has two calibration gaps 18a, 18b within the housing 1, the arrangement being such that light from the source unit 2 passes through the calibration gaps 18a and 18b into the photocell units 3a and 3b respectively when the units 2, 3a and 3b are retracted within the housing, and after the external surfaces of the light transmitting walls or windows of the units have been cleaned by respective O-rings 14 and 15a, 15b located in grooves in the housing 1.

I claim:

1. A photoelectric sensing head comprising a housing, a source unit and at least one photocell unit arranged side by side in the housing, each said unit having an enclosure with a light transmitting wall, wiping means within the housing which make wiping contact with the light transmitting walls of the enclosures, and means for displacing the enclosures relative to the housing to cause the wiping means to pass over external surfaces of the said light transmitting walls to clean them.

2. A sensing head as in claim 1, wherein the enclosures have cylindrical walls, the wiping means comprising resilient rings sealed in the housing and making contact with respective said light transmitting walls.

3. A sensing head as in claim 2, wherein two said photocell units are arranged on opposite sides of the source unit, the photocell units in operation of the head receiving light from the source unit through respective said light transmitting walls.

4. A sensing head as in claim 3, wherein the two photocell units are separated from the source unit by different distances to define gaps of different sizes which are traversed by light from the source unit in use of the head.

5. A sensing head as in claim 1, wherein the enclosures are movable between retracted positions within the housing and extended positions, projecting beyond the housing, in which said at least one photocell unit is separated from the source unit by a gap which is traversed by light from the source unit in use of the head.

6. A sensing head as in claim 5, wherein said at least one photocell unit is separated from the source unit by a calibration gap within the housing in the retracted positions of the enclosures.

7. A sensing head as in claim 6, wherein the housing is provided with seals contacting the surfaces of the enclosures within the housing at positions located on the other side of the respective calibration gap from the wiping means.

8. A sensing head as in claim 1, including means mechanically interconnected to the enclosures of the source unit and the at least one photocell unit for movement together by the displacement means.

9. A sensing head as in claim 8, wherein the means for displacing the enclosures comprises a reversible motor and a transmission member connected to the enclosures and displaceable by the said motor.

10. A sensing head as in claim 9, wherein the transmission member comprises a screw extending axially within the housing and engages a nut attached to the enclosures, so that rotation of the screw effects axial displacement of the enclosures relative to the housing, in a direction dependent upon the direction of rotation of the screw.

11. A sensing head as in claim 8, wherein the displacement means comprises a motor-driven crank mechanism and wherein the sensing head further includes a common support carrying the enclosures and displaceable by the crank mechanism.

12. A sensing head as in claim 1, wherein each enclosure has a removable end cap affording access to the interior of the enclosure.

13. A sensing head as in claim 1, wherein each enclosure has a cylindrical wall of transparent material.

14. A sensing head as in claim 1, wherein each enclosure has a cylindrical opaque wall in which a respective light transmitting window is provided, each said window having an outer part-cylindrical surface which is flush with the outer surface of the respective enclosure wall.

15. A sensing head according to claim 1 including a hinged boom supporting the housing at one end, and a turbidity measuring instrument electrically connected to the sensing head and carried at the other end of the boom.

16. A self-cleaning sensing head comprising a body having a sensing surface, a housing in which the body is mounted for relative displacement, wiping means within the housing making wiping contact with the sensing surface of the body, and powered means for displacing the body relative to the housing between a retracted position in which the sensing surface is within the housing and an extended position in which the sensing surface projects from the housing for immersion in a liquid, movement of the body between said positions causing the sensing surface to be wiped by the wiping means.

17. A sensing head as in claim 16, wherein the sensing surface is cylindrical and the wiping means comprises at least one resilient O-ring located within the housing and making wiping contact with the said sensing surface.

* * * * *